United States Patent [19]

Aguiar et al.

[11] 4,406,888
[45] Sep. 27, 1983

[54] AQUEOUS MICELLAR SOLUTIONS OF LEVONANTRADOL AND N-METHYLLEVONANTRADOL AND LYOPHILIC FORMS THEREOF FOR RECONSTITUTION

[75] Inventors: Armando J. Aguiar; Bijan Rasadi, both of Gales Ferry, Conn.

[73] Assignee: Pfizer Inc., New York, N.Y.

[21] Appl. No.: 223,672

[22] Filed: Jan. 9, 1981

[51] Int. Cl.³ .............................................. A61K 31/47
[52] U.S. Cl. .................................... 424/175; 424/258
[58] Field of Search ............................... 424/175, 258

[56] References Cited

U.S. PATENT DOCUMENTS 2,391,552  12/1945  Curtis ................................ 424/175
4,260,764   4/1981  Johnson ............................. 424/258
4,320,124   3/1982  Koe ................................... 424/258

FOREIGN PATENT DOCUMENTS 854655  11/1977  Belgium .

OTHER PUBLICATIONS

*Remington's Pharmaceutical Sciences,* Mack Publishing Company, Easton, Pennsylvania, 1980, pp. 1535 and 1565.
Remington's Pharmaceutical Sciences, 15th ed., Mack Publishing Company, (1975), pp. 283 and 320.

*Primary Examiner*—Delbert R. Phillips
*Assistant Examiner*—F. T. Moezie
*Attorney, Agent, or Firm*—Charles J. Knuth; Albert E. Frost; Allen Bloom

[57] ABSTRACT

Stable, aqueous micellar solutions of levonantradol and N-methyllevonantradol, especially useful for intramuscular administration, and lyophile formulations thereof suitable for reconstitution.

12 Claims, No Drawings

AQUEOUS MICELLAR SOLUTIONS OF LEVONANTRADOL AND N-METHYLLEVONANTRADOL AND LYOPHILIC FORMS THEREOF FOR RECONSTITUTION

BACKGROUND OF THE INVENTION

1. Field of the Invention

This invention relates to pharmaceutical preparations for parenteral use. More specifically, it relates to aqueous micellar solutions of the effective analgetic and antiemetic agents, levonantradol and N-methyllevonantradol, and to lyophile formulations of levonantradol and N-methyllevonantradol of improved stability which are of particular value for intramuscular administration of said analgetic agents.

2. Description of the Prior Art

Levonantradol, known chemically as [6S-[3S*,6-alpha,6a-alpha,9-alpha,10a-beta]]-5,6,6a,7,8,9,10,10a-octahydro-6-methyl-3-(1-methyl-4-phenylbutoxy)-1,9-phenanthridinediol 1-acetate, hydrochloride, and N-methyllevonantradol, the N-methyl derivative thereof, are effective analgetic and anti-emetic agents which are non-narcotic and free of addiction liability. Belgian Pat. No. 854,655, granted Nov. 16, 1977, describes the preparation and use of said compounds and their administration in composition form, said compositions including a pharmaceutical carrier selected on the basis of the chosen route of administration and standard pharmaceutical practice. Their administration in the form of tablets, pills, powders, capsules or granules containing excipients such as starch or milk sugar, or in the form of suspensions, solutions, emulsions, syrups and elixirs is also described therein.

Micellar solubilization of drugs which are insoluble in water or of low water solubility has been used to formulate clear aqueous solutions of such drugs. For example, incorporation of benzocaine into surfactant micelles to retard the rate of ester hydrolysis, and other pharmaceutical applications of micellar solubilization are described in Remington's Pharmaceutical Sciences, 15th Ed., Mack Publishing Company (1975), pages 283 and 320, respectively.

SUMMARY OF THE INVENTION

It has now been found that levonantradol and N-methylleveonantradol, both of which are subject to decomposition upon storage, particularly in solution, resulting in formation of colored by-products, loss of activity and, of course, economic loss, can be formulated into stable aqueous solutions by means of micellar solubilization, and in lyophile formulations, with the aid of a nonionic amphiphile as an essential component thereof.

As regards aqueous micellar solutions, such formulations are readily prepared by dissolving the active ingredient, i.e., levonantradol or N-methyllevonantradol, in a solution of the chosen amphiphile in less than the total volume of water to be present in the final formulation.

The active ingredient is generally, but not necessarily, used in the form of an acid addition salt, preferably the hydrochloride salt, which is easy to handle, relatively stable and which dissolves faster than does the free base form thereof. Following dissolution of the active ingredient, anti-oxidants, excipients and buffers are added, pH adjustments made, if necessary, and additional water added to achieve the desired concentration of active ingredient in the final formulation.

The aqueous micellar solutions thus prepared are clear solutions which are stable over relatively prolonged periods of time, and which give rise to rapid action of the active ingredient within the human body upon parenteral administration thereof. Levonantradol has been found to be completely stable in such solutions in accelerated stability studies for at least nine weeks at 37° C.

Lyophile formulations are prepared by lyophilization of aqueous micellar solutions and are reconstituted by addition of water.

DETAILED DESCRIPTION OF THE INVENTION

Aqueous micellar solutions of levonantradol or of N-methyllevonantradol, in reality of the free base form thereof by reason of the pH of said solutions, are prepared by adding the desired amount of a pharmaceutically acceptable acid addition salt of levonantradol or N-methyllevonantradol (active ingredient) to an aqueous solution of an appropriate non-ionic amphiphile (surfactant) in degassed, sterile water. Less than the final volume of water is, of course, used at this stage of the preparation in order to permit accurate make-up of the final solution to the desired concentration of active ingredient. As a matter of convenience, from about 40% to about 80% of the final volume of water required is used at this stage.

Any pharmaceutically acceptable acid addition salt of the active ingredient can be used. However, it is generally preferred to use the hydrochloride salt for reasons noted above.

While a great number of nonionic amphiphiles are known and useful in the formulations of this invention, for practical reasons, e.g., approval by regulatory agencies, the amphiphiles are generally chosen from the following types of nonionic amphiphiles: sorbitan fatty acid esters, polyoxyethylene sorbitan fatty acid esters, polyoxyethylene glycol esters and glyceryl fatty acid esters.

The preferred nonionic amphiphiles are polyoxyethylene sorbitan fatty acid esters and polyoxyethylene glycol fatty acid esters. Representative of polyoxyethylene sorbitan fatty acid esters are the mono oleate ester (sold under the trademark Polysorbate 80), the mono stearate ester (sold under the trademark Polysorbate 60), the mono laurate ester (sold under the trademark Polysorbate 20), and the tristearate ester (sold under the trademark Polysorbate 65), all of which are available from Atlas Chemical Industries, Inc. of Wilmington, Delaware.

Representative of the polyoxyethyleneglycol esters are polyoxyethylene (40) stearate (sold under the trademark Polyoxyl 40 Stearate), polyoxyethylene (8) stearate, polyoxyethylene (50) stearate (all of which are available from Atlas Chemical Industries); polyoxyethylene alcohol esters such as polyoxyethylene (23) lauryl ether, polyoxyethylene (10) cetyl ether, polyoxyethylene (20) stearyl ether and polyoxyethylene (20) oleyl ether (sold under the trademarks Brij 35, Brij 56, Brij 78 and Brij 98, respectively, and available from ICI United States, Inc., Wilmington, Delaware 19897).

The choice of a suitable nonionic amphiphile can be related to its hydrophile-lipophile balance number (HLB) as a first approximation. In general, amphiphiles having an HLB value of from about 11 to about 18 are especially useful in the formulations of this invention. Amphiphiles having an HLB value of from about 13 to about 17 are favored since they permit greater flexibility as regards the concentration of active ingredient for a given amount of amphiphile than do amphiphiles having HLB values outside the above cited range.

As those skilled in the art recognize, blends of nonionic amphiphiles, one having a high HLB value and the other a low HLB value, can be used to provide blends having an HLB value within the ranges cited above. In actual practice, however, the use of a single amphiphile is favored for the sake of convenience.

The concentration of amphiphile to be used varies with the individual amphiphile and with the active ingredient and is readily determined by experiment. It must, of course, be above the critical micelle concentration (cmc) of the chose amphiphile. It is known that the cmc of nonionic amphiphiles increases with increasing HLB value and may, depending on the amphiphile, increase or decrease with temperature. Sufficient amphiphile must, therefore, be present in the formulations of this invention to exceed the cmc over the temperature range to which said formulation may be exposed during its life time.

Since both levonantradol and N-methyllevonantradol exhibit reduced water solubility with decreasing temperature, the concentration of active ingredient in the formulation should not exceed the solubility thereof at the lowest temperature to which said formulation might be exposed. This temperature dependence of water solubilty of active ingredient is overcome by the use of sufficient concentration of amphiphile above the cmc such that the solubility of active ingredient is exceeded at said lowest temperature. The water solubility of active ingredients increases with increasing concentration above the cmc as is shown below for levonantradol in micellar solutions of Polysorbate 80 USP at pH 5.0 and 25° C. (Table I):

| % Polysorbate 80 USP (w/v) | Solubility (mg./ml.) of Levonantradol.HCl* 25° C., pH 5.0 |
|---|---|
| 0.0 | — |
| 0.1 | 0.0022 |
| 0.2 | 0.067 |
| 0.3 | 0.130 |
| 0.4 | 0.29 |
| 0.5 | 0.43 |
| 0.8 | 0.88 |
| 1.0 | 1.23 |
| 1.5 | 2.04 |
| 2.0 | 2.85 |
| 2.5 | 3.81 |
| 3.0 | 4.44 |
| 3.5 | 5.60 |
| 4.0 | 6.30 |
| 4.5 | 6.99 |
| 5.0 | 7.55 |
| 7.0 | 11.28 |

*Based on 88.8% activity.

Thus, it is seen that the water solubility of levonantradol (HCl salt) is markedly increased by the presence of a relatively low concentration of Polysorbate 80. This permits preparation of aqueous solutions of levonantradol which are able to deliver effective analgetic or antiemetic amounts thereof in relatively small volumes.

The cmc of a given amphiphile, if not known, is determined experimentally by measuring any one of several properties of an aqueous solution of varying concentration of said amphiphile, e.g., osmotic pressure, refractive index, surface tension, or solubility of a compound having low water solubility, e.g. levonantradol. At the cmc a plot of the measured property against amphiphile concentration exhibits a sharp change in slope.

The aqueous micellar solutions of this invention allow preparation of formulations which enable one to administer effective dose levels of active ingredient (levonantradol or N-methyllevonantradol) in minimum volumes of solution. From a practical standpoint such formulations having from about 0.01 to about 5.0 mg. of active ingredient (calculated as free base) are useful. Favored formulations are those having from about 0.1 to about 5 mg./ml. of active ingredient; and preferred formulations have from about 0.5 to about 2 mg./ml. thereof.

The herein described formulations of levonantradol and N-methyllevonantradol are especially valuable for parenteral administration of effective analgetic and antiemetic doses of said compounds. When used for said purposes sufficient formulation is administered to provide from about 0.005 to about 100 mg./day of said compounds in single or divided doses. The favored dosage range when formulations of this invention are used is from about 0.01 to about 50 mg./day; the preferred range is from about 0.01 to about 20 mg./day.

In order to prepare pharmaceutically elegant formulations it is advantageous, for optimum results, to add other substances, referred to as pharmaceutical necessities, thereto. Such substances include anti-oxidants or stabilizers, buffers, excipients, acids or bases to achieve a given pH value and, when said formulations are to be used parenterally, e.g. intramuscularly, substances to achieve isotonicity. These substances or pharmaceutical necessities should, of course, be pharmaceutically acceptable.

A wide variety of antioxidants are available and operative in the formulations of this invention. Representative antioxidants include sulfur-containing antioxidants such as thioglycerol, salts of sulfurous and hydrosulfurous acids and their aldehyde addition products, e.g., alkali metal bisulfites, metabisulfites and hydrosulfites. Favored antioxidants are sodium metabisulfite and sodium bisulfite. Said antioxidants are used in stabilizing amounts, i.e. from about 0.1% to about 2% (w/v).

The aqueous micellar solutions of this invention are desirably maintained within the pH range of about 4 to about 8 reasons of stability. The favored pH range is about 4 to about 7 and preferably about 5 to about 6. In order to achieve and maintain such pH values a nontoxic buffer is used. Suitable buffering agents are sodium citrate, sodium acetate, sodium dihydrogen phosphate and others known in the art. Sodium citrate is preferred since it appears to provide solutions of somewhat better stability than do sodium acetate or dihydrogen phosphate, although these agents are fully operative for said purpose. Sufficient buffer is, of course, used to maintain the desired pH. In practice from about 0.5 to about 5% of sodium citrate (w/v) is satisfactory. If another buffer is used, the amount thereof may be varied.

At the pH values at which the hereindescribed formulations are prepared (pH 4–8), levonantradol and N-methyllevonantradol exist to a great extent in their free base form. This is especially so as regards the preferred pH range of 5–6.

The use of a chelating agent such as ethylenediamine tetraacetic acid (EDTA) to inactivate polyvalent metal ions which may be present as impurities is sometimes of advantage. Concentrations of about 0.2% (w/v) of EDTA is sometimes beneficial.

The aqueous micellar solutions are rendered isotonic by addition of mannitol, sodium chloride or a mixture of chlorides of sodium, potassium and calcium.

Lyophile formulations of this invention are made by lyophilization of the hereindescribed aqueous micellar formulations. Of course, the aqueous micellar formulations need not be brought to final volume prior to lyophilization but can be lyophilized at the point in their preparation when all ingredients are in solution.

The lyophile formulations are readily reconstituted by addition of the required volume of water. Lyophile formulations are stored in tightly sealed amber vials under a nitrogen atmosphere.

The addition of a water miscible solvent, e.g. ($C_{1-4}$)alcohols, dioxane, tetrahydropyran; preferably ethanol to a formulation prior to lyophilization enables one to freeze dry the product while preventing the active ingredient from precipitating out of solution. The volume of solvent (ethanol) added is not critical. Sufficient ethanol should be used to prevent precipitation of the drug during lyophilization. The amount used should not, however, be so great as to prevent freezing of the mixture. Volumes of from about 10% to 30% by volume of ethanol are satisfactory.

The following examples are provided to illustrate this invention and are not to be interpreted as limiting the invention, the scope of which is defined by the appended claims.

In the examples, all percentages are expressed in standard weight by volume (w/v) terms.

EXAMPLE 1

This example illustrates preparation of a micellar solution having a concentration of 2 mg. levonantradol/ml. of solution which is of value for intramuscular administration of levonantradol. The overall composition of the formulation is:

|  | (w/v) |
|---|---|
| Levonantradol HCl | 0.2% |
| Polysorbate 80 USP | 2.0% |
| Mannitol | 3.5% |
| Sodium citrate | 0.25% |
| Sodium metabisulfite | 0.1% |
| Purified, degassed water to make pH 5.2 | 100% |

The procedure comprises dissolving the Polysorbate 80 USP in about 60% of the required water (previously degassed to remove dissolved air) at room temperature. The levonantradol hydrochloride was then added and the mixture stirred until solution was complete. The pharmaceutical necessities; i.e., mannitol, sodium citrate and sodium metabisulfite were then added together with about 20-25% of the remaining volume of water required. The pH was adjusted to 5.5 by addition of hydrochloric acid (10%) and the balance of water then added. The resulting formulation was made sterile by filtration and stored in amber vials sealed under a nitrogen atmosphere.

No loss of activity is observed after storage of the formulation for four weeks at 37° C. or 50 ° C.

The samples are analyzed for activity by a HPLC method using a Chromegabond C-8 column (silica silylated with octyltrichlorosilane, available from E. S. Industries, 8 South Maple Avenue, Marlton, N.J. 08053). The column is 4.6 mm I.D.×30 cm.; the mobile phase is 60% acetonitrile-40% phosphate buffer (0.05 M, pH 6.3) and the flow rate is 2 ml. per minute. Detection is by UV at 210 nm.

EXAMPLE 2

Following the procedure of Example 1, an aqueous micellar solution of levonantradol but in which mannitol was replaced by sodium chloride, was prepared. Its composition was:

|  | (w/v) |
|---|---|
| Levonantradol HCl | 0.2% |
| Polysorbate 80 USP | 2.0% |
| Sodium chloride | 0.6% |
| Sodium citrate | 0.25% |
| Sodium metabisulfite | 0.1% |
| HCl to pH 5.18 | |
| Water | q.s. |

Stability study of this formulation after 9 weeks storage in sealed amber ampoules ($N_2$ atmosphere) at 5°, 20°, 37° and 50° C., showed 102%, 102%, 100% and 98% of drug activity remained.

Repetition of the above procedure but replacing Polysorbate 80 by Polysorbate 60, Polysorbate 20 and Polysorbate 65 affords formulations of comparable stability.

EXAMPLE 3

Micellar solutions of levonantradol were prepared according to the procedure of Example 1.

|  | |
|---|---|
| Levonantradol HCl | 0.1% |
| Polysorbate 80 USP | 2.0% |
| Mannitol | 2.5% |
| Sodium citrate | 0.25% |
| Sodium metabisulfite | 0.1% |
| HCl to pH 5.2 | |
| Water | q.s. |

Stability of this formulation after storage in sealed amber ampoules at 5°, 20° and 50° C. for up to 16 weeks showed 101, 100 and 93% activity remained.

EXAMPLE 4

Ethanol (20% by volume) was added to formulations prepared according to Example 3 which were then lyophilized at −40° C. and the resulting lyophile stored in sealed type I amber vials (nitrogen atmosphere) at 5° C., room temperature (≈20° C.) 37° C. and 50° C. Analysis of the samples after 8 and 14 weeks storage gave the following data:

| % Levonantradol ||||||||
|---|---|---|---|---|---|---|---|
| 8 wks. |||| 14 wks. ||||
| 5° C. | 20° C. | 37° C. | 50° C. | 5° C. | 20° C. | 37° C. | |
| 102 | 101 | 99 | 101 | 100 | 102 | 99 | |

The samples are readily reconstituted by addition of water.

EXAMPLES 5

The procedure of Example 1 is repeated but using the following amounts of ingredients:

|  | % (w/v) | | | | |
| --- | --- | --- | --- | --- | --- |
|  | A | B | C | D | E |
| Levonantradol HCl | 0.025 | 0.1 | 0.15 | 0.3 | 0.5 |
| Polysorbate 80 USP | 0.5 | 1.0 | 2.0 | 3.0 | 5.0 |
| Mannitol | 3.5 | 3.5 | 3.5 | 3.5 | 3.5 |
| Sodium citrate | 0.25 | 0.25 | 0.25 | 0.25 | 0.25 |
| Sodium metabisulfite | 0.1 | 0.1 | 0.1 | 0.1 | 0.1 |
| HCl to pH 5.22 | | | | | |
| Water | q.s. | q.s. | q.s. | q.s. | q.s. |

The resulting formulations are comparable in stability to that of Example 1.

EXAMPLE 6

The procedure of Example 1 is repeated but substituting sodium bisulfite for sodium metabisulfite. The resulting formulations are comparable in stability to that of Example 1.

EXAMPLE 7

The procedure of Example 1 is repeated but replacing Polysorbate 80 USP with Polysorbate 20 and Polysorbate 60. The resulting formulations exhibit stability comparable to the formulation of Example 1.

EXAMPLE 8

The procedure of Example 1 is repeated but replacing levonantradol hydrochloride with N-methyl-levonantradol.

The resulting formulation is stable for at least four weeks in accelerated stability studies at 37° C. and 50° C.

Lyophilization of the formulation according to Example 4 affords a stable lyophile which is readily reconstituted by addition of water.

We claim:

1. A pharmaceutical composition comprising an aqueous micellar solution of (a) levonantradol or (b) N-methyllevonantradol, or a pharmaceutically acceptable acid addition salt of (a) or (b), as active ingredient, wherein (a) or (b) or salt of (a) or (b) is present at a concentration of from about 0.01 to about 5.0 mg/ml of (a) or (b); (c) at least a critical micelle concentration of a nonionic amphiphile selected from the group consisting of sorbitan fatty acid esters, polyoxyethylene sorbitan fatty acid esters, polyoxyethylene glycol esters and glyceryl fatty acid esters having a hydrophile-lipophile balance number of from about 11 to about 18, and (d) a stabilizing amount of an antioxidant of from about 0.1 to about 2% (w/v).

2. A composition according to claim 1 wherein the amphiphile is a polyoxyethylated nonionic amphiphile.

3. A composition according to claim 2 wherein the amphiphile is a polyoxyethylene sorbitan fatty acid ester.

4. A composition according to claim 3 wherein the fatty acid ester is the mono-oleate.

5. A composition according to claim 4 wherein the amphiphile is present at a concentration of from about 0.1 to about 5.0% (w/v).

6. A composition according to claim 6 wherein the amphiphile is present at a concentration of 2% (w/v) and the active ingredient is levonantradol, said ingredient being present at a concentration of 0.2% (w/v).

7. The composition according to claim 1 wherein the antioxidant is sodium metabisulfite.

8. A pharmaceutically acceptable lyophile formulation suitable for reconstitution comprising (a) levonantradol or (b) N-methyl-levonantradol or a pharmaceutically acceptable acid addition salt of (a) or (b), as active ingredients; (c) a nonionic amphiphile selected from the group consisting of sorbitan fatty acid esters, polyoxyethylene sorbitan fatty acid esters, polyoxyethylene glycol esters and glyceryl fatty acid esters having a hydrophilelipophile balance number of from about 11 to about 18, and (d) a stabilizing amount of an antioxidant; the amount of (a), (b) or a pharmaceutically acceptable salt of (a) or (b) present being such as to provide upon reconstitution with water, an aqueous solution wherein the active ingredient is present at from about 0.01 to about 5 mg./ml. of (a) or (b) and in which at least a critical micellar concentration of said amphiphile is present, and wherein upon reconstitution, the amount of (d) present is from about 0.1 to about 2% (w/v).

9. A formulation according to claim 8 wherein the active ingredient is levonantradol.

10. A formulation according to claim 9 wherein the amphiphile is a polyoxyethylene sorbitan fatty acid ester.

11. The formulation according to claim 10 wherein the fatty acid ester is the mono-oleate.

12. A formulation according to claim 11 wherein the antioxidant is sodium metabisulfite.

* * * * *